(12) United States Patent
Moliere

(10) Patent No.: US 8,656,769 B2
(45) Date of Patent: Feb. 25, 2014

(54) WIND TUNNEL FOR STUDYING VAPORIZATION OF LIQUIDS

(75) Inventor: Michel Moliere, Belfort (FR)

(73) Assignee: GE Energy Products France SNC (FR)

( * ) Notice: Subject to any disclaimer, the term of this patent is extended or adjusted under 35 U.S.C. 154(b) by 242 days.

(21) Appl. No.: 13/313,717

(22) Filed: Dec. 7, 2011

(65) Prior Publication Data

US 2012/0144911 A1    Jun. 14, 2012

(30) Foreign Application Priority Data

Dec. 8, 2010  (FR) ...................................... 10 60236

(51) Int. Cl.
*G01M 9/00*    (2006.01)
(52) U.S. Cl.
USPC .......................................................... 73/147
(58) Field of Classification Search
None
See application file for complete search history.

(56) References Cited

U.S. PATENT DOCUMENTS

| | | | | |
|---|---|---|---|---|
| 3,890,835 | A * | 6/1975 | Dotzer et al. | 73/147 |
| 3,896,666 | A * | 7/1975 | Johnson et al. | 73/147 |
| 5,421,171 | A * | 6/1995 | Wardle | 62/373 |
| 7,401,505 | B1 * | 7/2008 | Schultz et al. | 73/147 |

FOREIGN PATENT DOCUMENTS

| | | |
|---|---|---|
| EP | 1610125 A1 | 12/2005 |
| FR | 2694092 A1 | 1/1994 |

* cited by examiner

*Primary Examiner* — Lisa Caputo
*Assistant Examiner* — Jermaine Jenkins
(74) *Attorney, Agent, or Firm* — Global Patent Operation; Vivek P. Shankam

(57) ABSTRACT

A wind tunnel making it possible to measure the vaporization parameters of a test liquid exposed in a gas flow is disclosed. The wind tunnel comprises: a gas generator configured to generate a gas at a flow rate and at a temperature that are adjustable; a conditioning device designed to obtain a horizontal and uniform flow of the generated gas; a measurement chamber containing the liquid to be tested and various measurement devices making it possible to characterize the flow of gas passing through the measurement chamber; a tapping and analysis zone in which the gas-and-vapor mixture is tapped analyzed; and a discharge zone configured to discharge the gas-and-vapor mixture. The liquid to be tested in the tunnel presents a free surface positioned inside the measurement chamber in a manner such that it is swept continuously and tangentially by the uniform flow of gas.

10 Claims, 2 Drawing Sheets

WIND TUNNEL FOR STUDYING VAPORIZATION OF LIQUIDS

BACKGROUND OF THE INVENTION

1. Field of the Invention

Embodiments of the present invention relate to the evaporation of stagnant liquids under the effect of air streams and at variable temperature. This phenomenon covers a large number of practical situations, such as: evaporation in the open air, under the effect of wind, of static water surfaces, having areas of various sizes, such as, for example, ponds or swimming pools, manufacturing methods involving a vaporization process or the saturation of a gaseous phase; and evaporation of pools of liquid, either in the open air, or inside a ventilated enclosure. Such situation may correspond to leakage or to accidental spillage of liquid, the vapors of which present risks in terms of toxicity, fire, explosion or air pollution.

2. Description of the Prior Art

In thermal engineering, this very general phenomenon is designated by the expression "forced-convection vaporization", it being known that such a vaporization process that takes place predominantly under forced convection is very often accompanied by effects of natural-convection vaporization and of diffusion vaporization, which are the only phenomena present in an atmosphere that is completely still.

Knowledge of vaporization kinetics at the surfaces of pools of liquids is a growing need in process engineering and in the context of making industrial facilities safer. In this field, the regulations relating to the risks of fire and explosion associated with leakage of flammable substances in the form not only of gas clouds but also of pools of volatile liquids are becoming generally more stringent worldwide. Unfortunately, the current control of combustion phenomena does not make it possible, in real situations, to determine with sufficient accuracy and certainty the criteria for the transition from normal combustion conditions to deflagration conditions, or even to detonation conditions. In fact, the conditions that govern the development of a shock wave within structures as complex as those existing in industrial facilities, and under widely varying operating conditions, are not sufficiently controlled. Because of the lack of reliable predictive models, regulations remain highly restrictive, assuming that a risk of explosion exists whenever a pocket of gas or vapor appears and might ignite, i.e. whenever the concentration of the flammable substance in the pocket lies in the range extending from its lower flammability limit (LFL) to its upper flammability limit (UFL).

Methods have been developed in attempts to determine experimentally the vaporization kinetics of a flammable liquid under controlled conditions. For example, mention can be made of Patent FR 2 694 092 that relates to a method of measuring the rate of evaporation and the ignition time of a liquid fuel. In that method, a drop of fuel is formed and is placed in a surrounding gaseous environment; an image of the drop is taken on a plane optical receiver; the area of the image is measured over time; the area of the volume of the drop is calculated on the basis of the area of the image; and the temperature of the surrounding gaseous environment is measured simultaneously. That patent thus focuses on a method of monitoring how the volume of a drop of flammable substance in a surrounding gaseous environment varies over time, that variation being determined by means of an optical device.

Patent EP 1 610 125 describes a method of determining the vaporization properties of liquid fuels, for motor vehicle engines, that method having the particularity of using an electric heater element, immersed at least partially in the liquid, so as to conduct heat from the heater element to the liquid constituting the fuel. The invention described in that patent thus heats the fuel by means of heat transfer by conduction.

The methods described in the state of the art make it possible, experimentally, to approach the phenomenon of vaporization of a flammable liquid, but under specific conditions that do not necessarily reflect the real conditions encountered in industrial facilities. It then becomes difficult, or even dangerous, for the results obtained using those methods to be applied directly to real industrial situations, which present conditions that are quite remote from the experimental conditions that prevail in said methods. The vaporization kinetics of a liquid depend not only on the properties of said liquid, such as, for example, the composition and the specific volatility of each component, but also, and to a considerable extent, on the "aerothermal" conditions of the gaseous environment, which is often constituted by air. The term "aerothermal" as used in this document covers not only thermal conditions, such as temperature field, and air-flow conditions, such as velocity field and flow regime, characterized by the Reynolds number, but also the degree of vapor saturation of the gas, in particular its humidity, when the vapor is water vapor.

BRIEF SUMMARY OF THE INVENTION

According to one embodiment of the present invention, a wind tunnel making it possible to measure the vaporization parameters of a test liquid exposed in a gas flow is disclosed. The wind tunnel comprises, in a direction from an upstream portion of the wind tunnel to a downstream portion of the wind tunnel: a gas generator configured to generate a gas at a flow rate and at a temperature that are adjustable; a conditioning device designed to obtain a horizontal and uniform flow of the generated gas; a measurement chamber containing the liquid to be tested and various measurement devices making it possible to characterize the flow of gas passing through the measurement chamber; a tapping and analysis zone in which the gas-and-vapor mixture is tapped analyzed; and a discharge zone configured to discharge the gas-and-vapor mixture. The liquid to be tested in the tunnel presents a free surface positioned inside the measurement chamber in a manner such that it is swept continuously and tangentially by the uniform flow of gas.

BRIEF DESCRIPTION OF THE DRAWINGS

The accompanying drawings, which are incorporated in and constitute a part of the specification, illustrate one or more embodiments and, together with the description, explain these embodiments. In the drawings

DETAILED DESCRIPTION OF THE INVENTION

Figure 1:
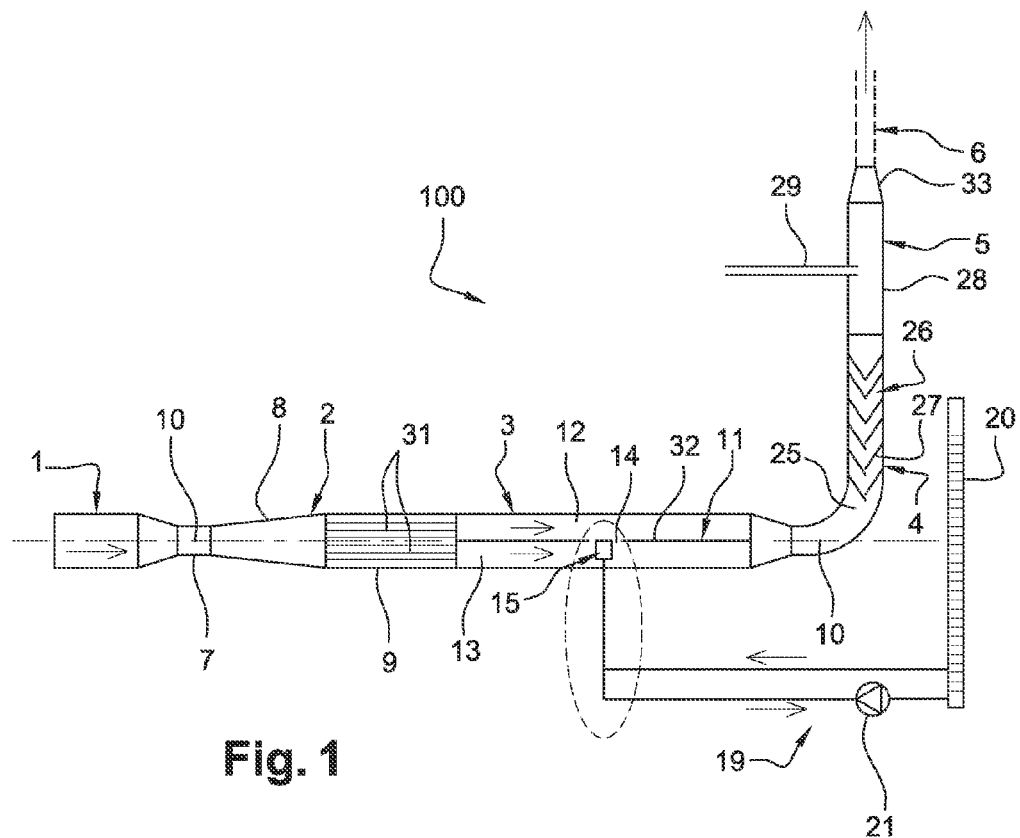
FIG. 1 is a diagrammatic view of an entire wind tunnel in accordance with an embodiment of the present invention.

In order to be able to conduct vaporization tests on a flammable liquid under conditions representative of the conditions encountered in as many real situations as possible, and with a view, in particular, to creating data bases, the Applicant has developed a wind tunnel that uses a flow of air and a pool of liquid, swept by the flow of air, and that offers all of the functions necessary for simulating a multitude of real situations. The particular design of the tunnel is aimed firstly, at controlling, rigorously and accurately, the parameters that govern the rate of vaporization of a liquid within a defined flow of air, which rate is characterized by the transfer coefficient of matter from the liquid phase to the vapor phase; the experimental results supplied by this tunnel are therefore reliable enough to be used in process or safety analyses, in particular for industrial facilities; and secondly, at knowing, in real time, the composition of the vapor flow; it is thus possible to calculate matter balances easily and accurately, and, for a flammable liquid, to determine the conditions under which the concentration of volatile materials exceeds the lower flammability limit.

The terms "upstream" and "downstream" should be interpreted relative to the movement direction of the air in the tunnel. In addition, the adjective "uniform" associated with terms such as "flow" or "stream" expresses the fact that both the velocity field and the temperature field are essentially uniform, i.e. the velocity vector and the temperature scalar are substantially identical at any point.

The main characteristic of a tunnel 100 of the invention is that the liquid to be tested presents a horizontal surface positioned inside the measurement chamber 3, in a manner such that it is swept continuously and tangentially by the uniform flow of gas. In this way, this specific interaction with the gas flow being tangential to the free surface of the liquid pool makes it possible to model real vaporization situations faithfully. By sweeping over the pool tangentially, the moving gas vaporizes the liquid substance to be tested, which substance then mixes with the gas. It should be noted that the resulting gas-and-vapor mixture formed downstream from the pool is not uniform in its volume, but rather it is stratified in the vertical direction, the vapor concentration decreasing from the top wall of the partition plate towards the top of the vaporization sub-chamber.

Implementing such a controlled vaporization interface offers the advantage of being able to determine rigorously the mass transfer coefficient that characterizes the vaporization kinetics. This coefficient, which depends only on the properties of the liquid and on the aerothermal characteristics of the flow of gas, is defined as the mass of liquid vaporized per unit time and per unit area divided by the difference between the mass concentration of vapor in the upstream gas and that immediately above the surface of the liquid. It should, in particular, be noted that, since this coefficient does not depend on the area of the pool, that area may be chosen quite arbitrarily. In order to cover a wide range of configurations, and with the objective of coming close to the real conditions of any industrial environment, the gas generator has means making it possible to generate the gas at a variable flow rate and at a variable temperature. The gas may be constituted by air. It may also be constituted by an inert gas, such as, for example, nitrogen, that can then be conveyed to the conditioning device, by connecting the nitrogen reservoir directly thereto. The gas generator may, for example, consist in an air fan with incorporated heating facility capable of bringing the emitted air to a high temperature. The measurement means installed inside the chamber make it possible to measure the aerothermal characteristics of the horizontal and uniform gas stream and passing through said chamber, namely, mainly: temperature; velocity; and flow regime. The liquid to be tested may be any flammable liquid, for instance gasoline.

In one embodiment, the measurement chamber 3 may have a horizontal partition plate 11 that has an opening 14 and that splits the measurement chamber 3 into: (i) a vaporization upper sub-chamber 12 having aerothermal sensors, and (ii) an auxiliary lower sub-chamber 13, also having aerothermal sensors, the tunnel 100 being shaped so that the gas coming from the conditioning device 2 passes simultaneously through both of the sub-chambers 12, 13, said measurement chamber 3 having a vaporization cell 15 that is filled with liquid and that has its top rim 17 positioned inside the opening 14 in the partition plate 11, in such a manner that the liquid comes at the same elevation as the top surface of the partition plate 11, and in such a manner that its free surface is in contact with the flow of air passing through the vaporization sub-chamber 12. The processes of mixing between the liquid vapors and the gas will occur only in the vaporization sub-chamber 12, close to the vaporization cell 15. The horizontal separation partition plate 11 between the two sub-chambers 12, 13 serves as a guide plane for guiding the flow of gas passing through the vaporization sub-chamber 12, so as to enable it to sweep over the surface of the liquid in strictly tangential manner.

The existence of the auxiliary sub-chamber 13 and the fact that it is also swept by the flow of gas satisfy two objectives. First, keeping the vaporization cell 15 and the liquid that flows therein at the same temperature as the gas flowing through the vaporization sub-chamber 12, and thereby securing isothermal vaporization, the liquid and the gas remaining at the same temperature. Second, securing flow symmetry between the two sub-chambers 12, 13. If the auxiliary sub-chamber 13 were not swept by the flow of gas, the asymmetry of the gas flow would degrade the uniformity quality of the stream in the vaporization sub-chamber 12, which would affect the quality of the vaporization rate measurements. The aerothermal sensors placed in the auxiliary sub-chamber 13 make it possible to evaluate accurately the flow-rate of gas passing through it, and its temperature, it being possible for these parameters to be compared directly with the parameters measured in the vaporization sub-chamber 12, and knowledge of the flow-rate in the auxiliary sub-chamber 13 being necessary in order to determine the balance of the vapors in the tapping zone 5, after the two streams meet.

The vaporization cell 15 may be fed continuously with liquid, by means of an independent external circuit 19 including a graduated reservoir 20 and a pump 21 having a low flow-rate and taking liquid from the graduated reservoir 20 and sending it to the vaporization cell 15. This continuous feeding is needed in order to maintain the free surface of the liquid constantly at the same elevation inside the vaporization cell 15, because the vaporization of the liquid tends to cause its level to drop. Thus, by monitoring, over time, the level of liquid in the graduated reservoir 20, it is possible to evaluate the quantity of liquid that has been transformed into vapor. In one embodiment, the liquid vaporization cell 15 has a level control system, designed so as to ensure that the liquid arriving continuously in the vaporization cell 15 does not overflow into the auxiliary sub-chamber 13.

A homogenization zone 4 may be arranged between the measurement chamber 3 and the tapping and analysis zone 5, in a manner such that the flow of gas passing through the vaporization sub-chamber 12 and that is charged with liquid vapor is mixed intimately with the vapor-free flow of gas coming from the auxiliary sub-chamber 13. In reality, the homogenization zone 4 has two effects, firstly to cause the intimate mixing of the liquid vapors with the flow of gas that has passed through the vaporization sub-chamber 12, and secondly to cause the intimate mixing of the two flows of gases coming respectively from the auxiliary sub-chamber 13 and from the vaporization sub-chamber 12. In one embodiment of the invention, in its upstream portion, this homogenization zone 4 has a cylindrical bend 25 having a cross-section smaller than the cross-section of the measurement chamber 3. This constricted bend procures the above-described dual mixing effect. In another embodiment of the invention, in its downstream portion, the homogenization zone 4 has a secondary mixing device 26, either of the dynamic type such as a small turbine of suitable size and driven by an external motor, or of the static type in the form of a straight cylindrical structure, in continuity with the bend 25, which structure consists in a series of internal shapes able to impart sharp changes to the gas flow passing through it and thus to achieve the full mixing between the gas and the liquid vapors. These internal shapes may take any form and, for example, may be constituted by stacks of balls, or plane deflectors, or may be mutually arranged such as to form baffles. The static type of secondary mixing may be used in an embodiment of the invention for reasons of simplicity of implementation.

The gas generator, the conditioning device 2, and the measurement chamber 3 may be limited by cylindroconical walls having a common axis of circular symmetry that is horizontal. This construction contributes to securing as well as possible the criterion of uniformity for the velocity field in the measurement chamber 3, and, by its simplicity of design, makes the overall assembly simpler and thus less costly to manufacture.

In another embodiment of the present invention, the tapping and analysis zone 5 may limited by a cylindrical wall 28, the mixture of gas and of liquid vapor being tapped continuously by means of a radial tube 29 opening out in said wall 28 and sending the tapped fraction to instruments for analyzing the vapors of the vaporized liquid. In order to avoid disturbing the gas flow in the tapping zone, the radial tube 29 is of small section, and the tapped volume is small.

In another embodiment of the present invention, in the zone provided for that purpose, the mixture of gas and of vaporized liquid is tapped discontinuously, at predefined time intervals. The time intervals are arbitrary and are defined depending on the needs of the tests. For this configuration, the tapping may, for example, be performed by means of a syringe, either used manually by an operator, or controlled automatically at pre-programmed time intervals.

The tunnel 100 may be made of a transparent material. For example, the transparent material may be constituted by ordinary glass or by borosilicate glass, or indeed by silica glass, if improved resistance to thermal shocks is desired. Such transparent walls make it possible to see all of the phenomena taking place inside the wind tunnel 100, in particular inside the vaporization sub-chamber and inside the vaporization cell 15, and thus make it possible to verify the progress of the operation in full, thereby enabling the operating conditions to be better controlled. The glass makes it possible to work at relatively high temperatures, and, as a result to its low thermal conductivity, to reduce heat losses, thereby avoiding the need to insulate the tunnel 100 thermally in order to control its temperature and preserving full visibility for observing the phenomena.

The tunnel 100 may miniaturized, its weight being less than 10 kilograms (kg). Also, the footprint of the tunnel 100 may be less than 1 square meter ($m^2$).

The term "miniaturized" means that the dimensions of the tunnel 100 are small, the measurement chamber 3 diameter lying, for example, in the range 10 centimeters (cm) to 20 cm. This miniaturization offers the following advantages: absence of risk of explosion and of fire during the experiments; small footprint and low cost; gas generator having a low flow rate and low energy consumption; low unit cost of measurements; volume of test liquid very small, generating low cost for procurement and for disposal at the end of the testing; and rapidity of handling, useful, in particular, for executing large series of experiments.

With reference to FIG. 1, a tunnel 100 of an embodiment of the invention is made up of a plurality of elements situated one after another, with, in the following order: an air generator 1, a conditioning device 2 designed to form a horizontal and uniform flow from the flow of air emitted by said generator 1, a measurement chamber 3, a homogenization zone 4 for homogenizing the vapor and the air, a tapping and analysis zone 5 for tapping and analyzing the air-and-vapor mixture, and finally, a discharge zone 6 for discharging the air-and-vapor mixture. The tunnel 100 is miniaturized, and the main dimensional parameters resulting from the miniaturization mean that its footprint does not exceed 1 $m^2$, and that its weight is less than 10 kg.

The air generator 1 is a small-size air fan preferably having heating incorporated therein, and capable of delivering a horizontal flow of air at adjustable flow rate and at adjustable temperature. Typically, the fan 1 can deliver a flow of air having a temperature that can reach 200° C. The conditioning device 2 includes a flow tranquilizer device 7 serving to eliminate the turbulent components of the flow coming from the fan 1, and optionally a diffuser 8 extending said tranquilizer device 7 and constituted by (i) a convergent cone or by a divergent cone of horizontal axis and having a small angle, and (ii) a lamination device 9 configured to generate a flow of air that is horizontal and uniform. The tranquilizer device 7, which is embodied by a cylindrical part of small diameter, is designed to make the flow irrotational at the outlet of the fan 1, both by destroying any coherent rotational movement of the air, and by breaking up the non-steady vortices generated by the rotor of the fan 1. To this end, it is possible to lay across the flow section a layer of a material consisting of fibers or filaments that are woven or non-organized, and that break up the vortices and the coherent rotational movements. In order to minimize pressure loss, it is possible to use fibers or filaments of diameters of about one millimeter (mm), resulting in a spaced-out texture, such as steel wool, and preferably stainless steel wool. The diffuser 8 is an optional part made necessary when the cross-section dimension of the tranquilizer device 7 is different from the cross-section dimension of the measurement chamber 3. This diffuser 8 is a convergent or divergent conical part having a cone angle that is typically less than 10°, making it possible to form a junction between the tranquilizer device 7, which has a diameter that depends on the size of the air generator 1, and the lamination device 9, which is a cylindrical part of diameter identical to the diameter of the measurement chamber 3. The lamination device 9 is made up of a plurality of parallel and horizontal longitudinal mini-channels 31, said mini-channels 31 touching each other over their length, and having small cross sections. Advantageously, the inside diameter of said mini-channels 31 lies approximately in the range 5 mm to 6 mm. The length of said mini-channels 31 is sufficiently long to establish, at the inlet of the measurement chamber 3, a flow of air that is horizontal and uniform, such a mini-channel length typically being greater than 4 times the diameter of the measurement chamber 3. The measurement chamber 3 is a horizontal cylindrical part. The tranquilizer device 7, the diffuser 8, the lamination device 9, and the measurement chamber 3 share a common axis 10 of circular symmetry that extends horizontally. In other words, the tranquilizer device 7, the diffuser 8, the lamination device 9, and the measurement chamber 3 are fully aligned in a horizontal direction. The measurement chamber 3 has a horizontal median partition plate 11 in the form of a rectangular plate of small thickness, having top and bottom faces that are totally smooth, and it serves to split the measurement chamber 3 into a vaporization upper sub-chamber 12 and an auxiliary lower sub-chamber 13, these two sub-chambers 12, 13 being symmetrical to each other about the partition plate 11. The air coming from the lamination device 9 located upstream from the measurement chamber 3 flows through the two sub-chambers 12 and 13 at substantially identical flow rates that can be determined by their respective sets of velocity and temperature sensors. The median partition plate 11 has a circular opening 14 that has its center situated on the axis 10 of symmetry, and that enables the two sub-chambers 12 and 13 to communicate with each other.

Figure 2:
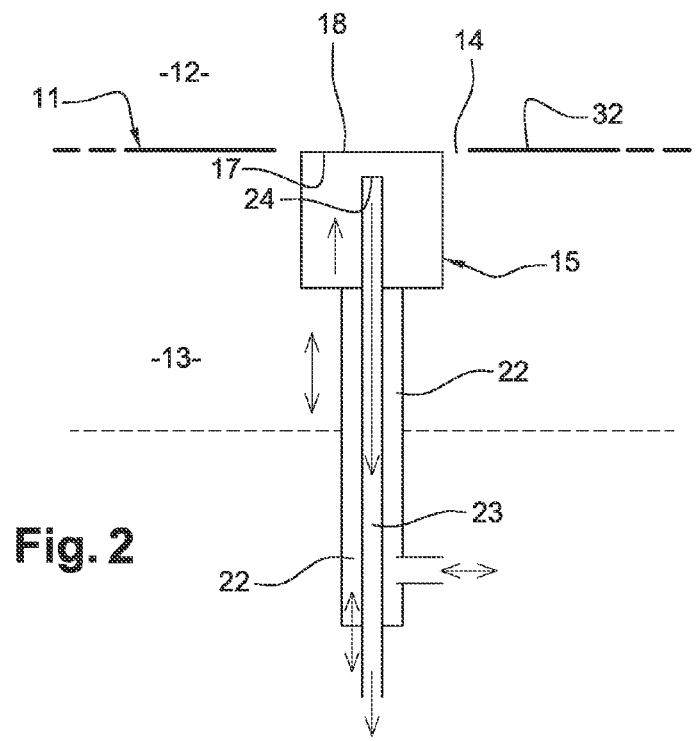
FIG. 2 is a diagrammatic view of a vaporization cell used in a wind tunnel in accordance with an embodiment of the present invention.

With reference to FIG. 2, the opening 14 in the median partition plate 11 is designed to host a vaporization cell 15 that contains the liquid to be vaporized and that is equipped with a thermocouple for monitoring the temperature of said liquid. This vaporization cell 15 is a hollow cylindrical part that can have a capacity of about 5 milliliters (ml), and that is of diameter slightly smaller than the diameter of the opening 14 in the partition 11, the maximum clearance between said opening 14 and the vaporization cell 15 not exceeding 1 mm. The vaporization cell 15, which is open at its top 17, is contained in the auxiliary sub-chamber 13. The bottom of the vaporization cell 15 is assembled to a vertical tubular fitting 22 that has the same axis of circular symmetry and that is mostly contained within the auxiliary sub-chamber 13, but that passes through the bottom wall of said auxiliary sub-chamber 13 through a leak-tight junction enabling it to move in vertical translation. In this way, the assembly constituted by the vaporization cell 15 and by the tubular fitting 22 can thus be moved vertically in such a manner that the top rim 17 of the vaporization cell 15 at the same elevation as the level of the top plane 32 of the partition plate 11. In other words, when the vaporization cell 15 is completely full of liquid, the free surface 18 of said liquid finds itself exactly contained in the top plane 32 of the partition 11. Thus, the flow of air that comes from the laminating device 9, and that penetrates into the vaporization sub-chamber 12 with a velocity field that is uniform and horizontal, firstly keeps the same velocity field characteristics upstream from the free surface 18 of the liquid, because it is bound to sweep over the partition 11, which is totally plane, horizontal, and smooth, and secondly, therefore, sweeps over the free surface 18 of the liquid in totally tangential manner. Since a fraction of the liquid present in the vaporization cell 15 is evaporated into the flow of air passing through the vaporization sub-chamber 12, it is necessary to feed the vaporization cell 15 continuously with liquid, so as to maintain the surface 18 of said liquid at the same level as the top plane 32 of the partition plate 11. The minimum feed flow-rate that is required is low, because it just needs to compensate for the vaporization of the liquid. This feeding takes place in a closed circuit 19 via an independent external circuit 19 including a graduated reservoir 20 and a low-flow pump 21. The liquid taken from the reservoir 20 is pumped to the tubular fitting 22, inside which it rises so as to flow into the vaporization cell 15, and the non-vaporized fraction is removed, in a downward movement, via a hollow tube 23 that passes through the vaporization cell 15 and through the tubular fitting 22, through a leaktight junction enabling it to move in vertical translation, independently of the assembly constituted by the vaporization cell 15 and by the tubular fitting 22. The hollow tube 23 may thus be positioned vertically, in such a manner that its top end 24 finds itself at an elevation slightly lower than the elevation of the top rim 17 of the vaporization cell 15, so as to prevent a possible meniscus effect from causing the liquid to spill out from the vaporization cell 15. This hollow tube 23 serves thus as an overflow device for the liquid of the cell, and thus as a means to control the level of liquid in the vaporization cell 15.

Implementing this device therefore consists firstly in positioning the top rim 17 of the vaporization cell 15 exactly in the top plane 32 of the partition plate 11, and secondly in keeping the vaporization cell 15 continuously full of liquid, so that the free surface 18 of said liquid finds itself exactly and constantly contained in the top plane 32 of the partition plate 11, and is swept in exactly tangential and continuous manner by the horizontal and uniform flow of air.

The drop in the level of the liquid that is monitored, over time, in the graduated reservoir 20, gives information about the volume of liquid that has evaporated in contact with the flow of air passing through the vaporization sub-chamber 12, given that it is necessary also to take account of the identical and concomitant drop in level that takes place in the hollow tube 23 by the communicating-vessels effect. The hollow tube 23 thus has a calibrated inside diameter.

The homogenization zone 4 for homogenizing the vapor and the air is situated downstream from the measurement chamber 3 and in continuity therewith. The homogenization zone 4 is necessary to have the flow of vapor-enriched air coming from the vaporization sub-chamber 12 mixed intimately with the vapor-free air flow coming from the auxiliary sub-chamber 13. This zone is embodied, in its upstream portion, by a cylindrical bend 25 of diameter smaller than the diameter of the measurement chamber 3, and, in its downstream portion, by a secondary mixing device 26, preferably of the static type, in the form of a straight cylindrical compartment in continuity with the bend 25. This compartment 26 consists in a series 27 of internal shapes able to impart sharp changes to the flow lines, which changes are designed to achieve full mixing. These internal shapes may take any form, and may, for example, be formed by stacks of balls, or by a series of deflector surfaces. They may also be mutually arranged to form baffles. However, all of these internal shapes must be dimensioned so that together they do not generate an excessive pressure loss. The bend 25 is a right-angled bend, so that the axis of the additional static device 26 is perpendicular to the axis 10 of the measurement chamber 3, and extends upwards. The secondary mixing device 26 is extended by the tapping and analysis zone 5 for tapping and analyzing the intimate mixture of air and of liquid vapor, this zone 5 being limited by a cylindrical wall 28 having the same diameter as the secondary mixing device 26, and in continuity therewith. In a first embodiment of a tunnel 100 of the invention, the mixture of air and of vaporized liquid is tapped continuously by means of a radial tube 29 of small diameter that passes through said wall 28 and that sends the tapped fraction towards measurement instruments continuously, making it possible to determine the concentration of the vaporized liquid in the air. This fraction may also be sent towards a condensation trap, e.g. a dry-ice trap or a liquid-nitrogen trap, for deferred overall analysis. In a variant embodiment of a tunnel 100 of the invention, in the zone 5 provided for that purpose, the mixture of air and of vaporized liquid is tapped discontinuously, at predetermined time intervals. For this configuration, the tapping may, for example, take place by means of a syringe, either used manually by an operator, or controlled automatically at pre-programmed time intervals. For flammable liquids, it is also possible to use an explosimeter that, in real time, gives the vapor concentration or the vapor-mixture concentration, expressed as a percentage of the LFL of the vapor or of the vapor mixture.

For measuring the evaporation of water, the measurement instrument may be an infrared analyzer. For measuring the evaporation of an organic substance constituted by a single pure species, the measurement instrument may comprise an infrared analyzer, or a Flame Ionization Detector (FID), or any other type of detector to which the vapors are sensitive (Thermal Conductivity Detector (TCD), Photoionization Detector (PID), etc.). For a mixture of a plurality of organic pure species, the measurement instrument may implement a gas chromatography separation column followed by a suitable detector, or even a mass spectrometer.

The discharge zone 6 for discharging the vapor-and-air mixture is constituted by a tube 30 extending the cylindrical wall 28 of the tapping and analysis zone 5, it being possible for the diameter of said tube 30 to be smaller than the diameter of said wall 28. A convergent cone 33 makes it possible to connect the wall 28 of the analysis zone 5 to the discharge tube 30.

The secondary mixing device 26, the tapping and analysis zone 5, the convergent cone 33, and the discharge tube 30 may share a common axis of circular symmetry. In other words, the secondary mixing device 26, the tapping and analysis zone 5, the convergent cone 33, and the discharge tube 30 are in alignment in a direction perpendicular to the horizontal direction in which the tranquilizer device 7, the diffuser 8, the laminating device 9, and the measurement chamber 3 are aligned. Preferably, this direction is vertical, so as to reduce the footprint.

The tunnel 100 is made of a transparent material. The transparent material may, for example, be an ordinary glass or a borosilicate glass, or even silica glass, if improved resistance to thermal shock is desired. Such transparent walls make it possible to see all of the phenomena taking place inside the tunnel 100, in particular, inside the vaporization sub-chamber 12 and inside the vaporization cell 15, and thus make it possible to verify the progress of the operation in full, thereby enabling the operating conditions to be better controlled. The glass makes it possible to work at relatively high temperatures, and, as a result of low thermal conductivity, to reduce heat losses, thereby avoiding the need to insulate the tunnel 100 thermally in order to control its temperature.

The small dimensions of the tunnel of the invention make it possible to use a small quantity of liquid for conducting the tests, thereby strongly limiting, or even suppressing, the risk of any deflagration or detonation occurring in said tunnel and also limiting the effects thereof. In this way, the risks of potential damage being done to property or people are reduced, or even suppressed.

In variant embodiments of a tunnel 100 of the invention, the cylindro-conical geometrical shape mentioned in the description may, for example, be replaced with a prismatic geometrical shape.

In addition, it is possible to conduct the vaporization process not only under isothermal conditions, as described in the above embodiment, but also either under quasi-adiabatic conditions, by requiring a minimum liquid re-circulation flow-rate in the circuit 19, and by using a vaporization cell 15 and a tubular fitting 22 made of an insulating material, of quite large thickness, such as a plastics material such as Teflon; or while having a gas temperature and a liquid temperature that are different, which, for the liquid fraction, can be achieved by using a small heat exchanger, optionally provided with temperature regulation, and installed upstream from the tubular fitting 22.

Figure 3:
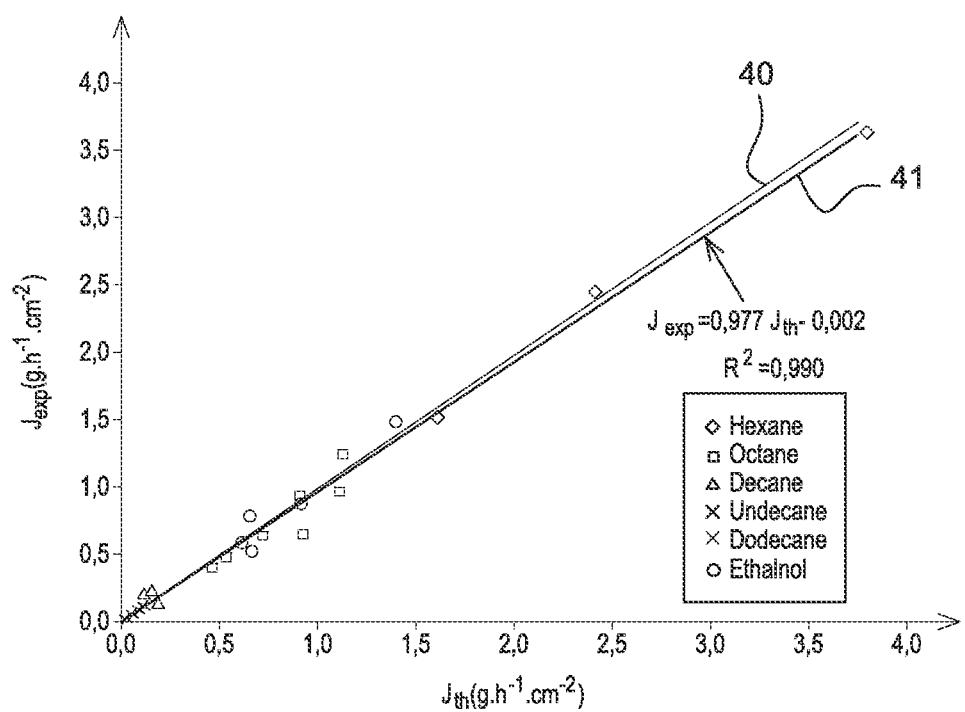
FIG. 3 is a graph showing the correlation between the rates of vaporization of some liquids as obtained firstly experimentally using a tunnel in accordance with an embodiment of the present invention and secondly theoretically.

FIG. 3 is a graph comparing the mass-per-unit-area vaporization rates, denoted as data "J", and expressed in grams per hour per square centimeter (g/h/cm2), which rates are obtained firstly experimentally with a set of hydrocarbons and ethanol, using the tunnel 100 of the invention, the rates being shown by the curve 40; and secondly theoretically, by means of a calculation based on M. Pauken's model (Reference: Michael Pauken, "An experimental investigation of combined turbulent free and forced evaporation", Experimental Thermal and Fluid Science 18, 1999, 334-340), that has been created on the basis of vaporization measurements taken on water implemented in a large-size reservoir, the corresponding data being represented by the curve 41.

It is easy to see that there exists a good agreement between the two series 40 and 41 of values, despite the large span of the vaporization rates covered (nearly three decades). This particular example shows how the use of the tunnel 100 has made it possible to show, in less than one week of tests, that the theoretical model developed by M. Pauken for water applies to other liquids under certain conditions of temperature and velocity, by modifying the appropriate physico-chemical parameters, and that it is slightly conservative, which is preferable in the context of safety investigations.

The wind tunnels according to embodiments of the present invention offer the advantage of being able to reproduce the conditions of a real environment, while also having simplified geometry, in the form of assemblies of cylindroconical tubes, and are thus easy to manufacture, to assemble, and to disassemble. In addition, when the tunnels of the invention are miniaturized, they offer the advantage of facilitating any action, operation, or handling by an operator using them for the conduction of vaporization tests. This results in non-negligible time-saving, and in good control of the operating conditions, imparting simplicity, great reliability, and good reproducibility to the tests conducted.

What is claimed is:

1. A wind tunnel making it possible to measure the vaporization parameters of a test liquid exposed in a gas flow, and the wind tunnel comprising, in a direction from an upstream portion of the wind tunnel to a downstream portion of the wind tunnel:
   a gas generator configured to generate a gas at a flow rate and at a temperature that are adjustable;
   a conditioning device designed to obtain a horizontal and uniform flow of the generated gas;
   a measurement chamber containing the liquid to be tested and various measurement devices making it possible to characterize the flow of gas passing through the measurement chamber;
   a tapping and analysis zone in which the gas-and-vapor mixture is tapped analyzed; and
   a discharge zone configured to discharge the gas-and-vapor mixture,
   wherein the liquid to be tested in the tunnel presents a free surface positioned inside the measurement chamber in a manner such that it is swept continuously and tangentially by the uniform flow of gas.

2. The wind tunnel according to claim 1, wherein the measurement chamber comprises a horizontal partition plate comprising an opening,
   wherein the partition plate splits the measurement chamber into a vaporization upper sub-chamber comprising aerothermal sensors, and an auxiliary lower sub-chamber comprising aerothermal sensors,
   wherein the tunnel is shaped such that gas coming from the conditioning device passes simultaneously through both of the sub-chambers, and wherein the chamber comprises a vaporization cell that is filled with liquid and that has its top rim positioned inside the opening in the partition plate in such a manner that the surface of the liquid comes to the same elevation as the top surface of the partition plate, and in such a manner that the free surface of the liquid is in contact with the flow of air passing through the vaporization sub-chamber.

3. The wind tunnel according to claim 2, wherein the vaporization cell is fed continuously with liquid by an independent external circuit comprising a graduated reservoir and a pump comprising a low flow-rate and configured to take liquid from the graduated reservoir and send it to the vaporization cell.

4. The wind tunnel according to claim 2, further comprising a homogenization zone arranged between the measurement chamber and the tapping and analysis zone such that the flow of gas that passes through the vaporization sub-chamber is mixed intimately with the vapor-free flow of gas that passes through the auxiliary sub-chamber.

5. The wind tunnel according to claim 1, wherein the gas generator, the conditioning device, and the measurement chamber are delimited by cylindroconical walls having a common and horizontal axis of circular symmetry.

6. The wind tunnel according to claim 1, wherein the tapping and analysis zone is delimited by a cylindrical wall, the mixture of gas and of liquid vapor being tapped continuously by a radial tube opening out in the cylindrical wall, and sending the tapped fraction to instruments for analyzing the vapors of the vaporized liquid.

7. The wind tunnel according to claim 1, wherein, in the zone, the mixture of gas and of vaporized liquid is tapped discontinuously, at predefined time intervals.

8. The wind tunnel according to claim 1, wherein the tunnel is made of a transparent material.

9. The wind tunnel according to claim 1, wherein the tunnel is miniaturized, and weighs less than about 10.0 kg.

10. A wind tunnel according to claim 9, wherein the footprint of the tunnel is less than 1 $m^2$.

* * * * *